United States Patent
Parker et al.

[11] Patent Number: 5,488,068
[45] Date of Patent: Jan. 30, 1996

[54] AMINOBIPHENYL-4-OL ANTI-ATHEROSCLEROTIC COMPOUNDS AND METHOD

[75] Inventors: Rex A. Parker, Lawrenceville; Scott A. Biller, Ewing, both of N.J.

[73] Assignee: Bristol-Myers Squibb Company, Princeton, N.J.

[21] Appl. No.: 292,671

[22] Filed: Aug. 18, 1994

[51] Int. Cl.$^6$ .................................................. A61K 31/135
[52] U.S. Cl. .......................................... 514/647; 564/307
[58] Field of Search ............................. 564/307; 514/647

[56] References Cited

U.S. PATENT DOCUMENTS

| | | | |
|---|---|---|---|
| 1,856,131 | 5/1932 | Grether | 564/307 |
| 4,022,911 | 5/1977 | Goldhaft et al. | 424/329 |
| 4,072,700 | 2/1978 | Bohler et al. | 260/438.1 |

FOREIGN PATENT DOCUMENTS 0515684  12/1992  European Pat. Off. .

OTHER PUBLICATIONS

Sharma et al., Chemical Abstracts, vol. 93 (1980) 245607b.
Beecham Group, Chemical Abstracts, vol. 106 (1987) 119442t.
Hoppe et al., Chemical Abstracts, vol. 108 (1988) 39660p.
Sparrow, C. P. et al, "Low density Lipoprotein is Protected from Oxidation and Progressin of Atherosclerosis is Slowed in Cholesterol–fed Rabbits by the Antioxidant N,N'–Diphenyl–Phenylenediamine", J Clin. Invest., vol. 89, Jun. 1992, 1885–1891.
Bjorkhem, I., et al, "The Antioxidant Butylated Hydroxytoluene Protects Against Atherosclerosis", Arteriosclerosis and Thrombosis, vol. 11, No. 1, Jan./Feb. 1991, pp. 15–22.
Kita, T., et al, "Probucol prevents the progression of atherosclerosis in Watanabe heritable hyperlipidemic rabbit, an animal model for familial hypercholesterolemia", Proc. Natl. Acad. Scir. USA, vol. 84, pp. 5928–5931, Aug. 1987, Medical Sciences.
Carew, T. E., et al, "Antiatherogenic effect of probucol unrelated to its hypocholesterolemic effect: Evidence that antioxidants in vivo can selectively inhibit low density lipoprotein degradation . . . " Proc. Natl. Acad. Sci. USA, vol. 84, pp. 7725–7729, Nov. 1987, Medical Sciences.

*Primary Examiner*—Richard L. Raymond
*Attorney, Agent, or Firm*—Burton Rodney

[57] ABSTRACT

Antiatherosclerotic compounds are provided which have the structure

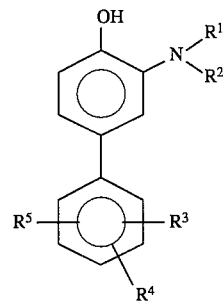

wherein $R^1$ and $R^2$ are independently hydrogen, lower alkyl, or arylalkyl, at least one of $R^1$ and $R^2$ being other than hydrogen, and $R^3$, $R^4$ and $R^5$ are independently hydrogen, lower alkyl, lower alkenyl, halo, alkoxy, aryl or arylalkyl. A method for treating atherosclerosis employing the above compounds is also provided.

6 Claims, No Drawings

AMINOBIPHENYL-4-OL ANTI-ATHEROSCLEROTIC COMPOUNDS AND METHOD

FIELD OF THE INVENTION

The present invention relates to 3-substituted aminobiphenyl-4-ol compounds which are LDL antioxidants and thus useful in treating atherosclerosis.

BACKGROUND OF THE INVENTION

Low density lipoprotein (LDL) lipid oxidation products promote atherogenesis by stimulating an inflammatory response in vascular tissue (refs. 1–3). A spectrum of oxidized LDL species contributes to the pathobiology of the atherogenic environment within the arterial wall. Products forming early in the process of LDL oxidation promote expression of inflammatory cytokines, cell adhesion molecules, and chemotactic and growth factors, leading to monocyte influx and macrophage foam cell formation in the arterial intima (refs. 2,3). Extensively oxidized LDL promotes expression of scavenger receptors on macrophages, accelerating foam cell formation, leading to entrapment of highly oxidized LDL within the artery wall, and resulting in cytotoxicity and endothelial dysfunction (ref. 4).

The presence of oxidized LDL within atherosclerotic lesions in a rabbit model and in humans has been demonstrated (refs. 4,5). At high doses the antioxidant probucol decreased arterial lesion size in animal models of atherosclerosis, and these effects were correlated with the ability of probucol to decrease oxidation of LDL in vivo (refs. 6,7). Lipophilic antioxidants such as butylated hydroxytoluene (BHT) and N,N'-diphenylphenylenediamine (DPPD) have been shown to decrease aortic lesions in rabbits and protect LDL from oxidation (refs. 8,9).

REFERENCES

1. Steinberg, D. "Lipoproteins and the pathogenesis of atherosclerosis", (1987) Circulation 76: 508–514.

2. Berliner, J. A., et al "Minimally modified low density lipoprotein stimulates monocyte endothelial interactions", (1990) J. Clin. Invest. 85: 1260–1266.

3. Cushing, S. D., et al "Minimally modified low density lipoprotein induces monocyte chemotactic protein 1 in human endothelial cells and smooth muscle cells", (1990) Proc. Nat'l. Sci. U.S.A. 87: 5134–5138.

4. Yla-Herttuala, S., et al "Evidence for the presence of oxidatively modified LDL in atherosclerotic lesions of rabbit and man", (1989) J. Clin. Invest. 84: 1086–1095.

5. Palinski, W., et al "Low density lipoprotein undergoes oxidative modification in Vivo", Proc. Natl. Acad. Sci. U.S.A. 1989; 86: 1372–1376.

6. Kita, T., et al, "Probucol prevents the progression of atherosclerosis in WHHL rabbits", Proc. Natl. Acad. Sci. U.S.A., 1987; 84: 5928–5931.

7. Carew, T. E., et al, "Antiatherogenic effect of probucol unrelated to its hypocholesterolemic effect: evidence that antioxidants in vivo can selectively inhibit LDL degradation in macrophages and slow the progression of atherosclerosis in the WHHL rabbit", Proc. Natl. Acad. Sci. U.S.A., 1987; 84: 7725–7729.

8. Bjorkhem, I., et al, "The antioxidant butylated hydroxytoluene protects against atherosclerosis", Arterioscler. Thromb., 1991; 11: 15–22.

9. Sparrow, C. P., et al, "Low density lipoprotein is protected from oxidation and the progression of atherosclerosis is slowed in cholesterol-fed rabbits by the antioxidant N,N'-diphenylphenylenediamine", J. Clin. Invest., 1992; 89: 1885–1891.

European Patent Application D515684A1 discloses inhibitors of denatured LDL formation which may have the formula

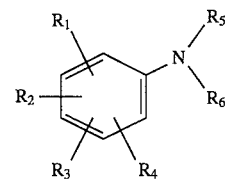

wherein $R_1$, $R_2$, $R_3$ and $R_4$ are selected from H, OH, optionally branched alkyl, alkoxy, methylthio, trimethylsilyloxy, methylenedioxy, halogen and phenyl; $R_5$ can be

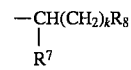

where k is 0 to 8 and $R_7$ can be H, $R_8$ can be optionally branched alkyl, optionally branched alkenyl, optionally substituted phenyl, optionally substituted heterocyclic, cycloalkyl, naphthyl, adamantyl, tosyloxy, hydroxy or $CO_2R_9$ where $R^9$ is H or alkyl;

$R_6$ is H, alkyl or $-(CH_2)_nR_{13}$ where n is 1 to 6 and $R_{13}$ is OH, optionally substituted phenyl, cyclohexyl or optionally substituted carboxyl.

DESCRIPTION OF THE INVENTION

In accordance with the present invention, aminobiphenyl-4-ol compounds are provided having the formula I

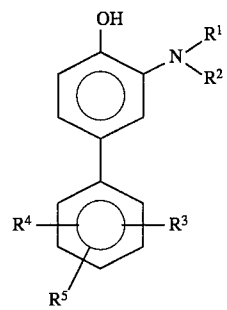

wherein $R^1$ and $R^2$ are independently hydrogen, lower alkyl, or arylalkyl, at least one of $R^1$ and $R^2$ being other than hydrogen; and $R^3$, $R^4$ and $R^5$ are independently hydrogen, lower alkyl, halo, alkoxy, lower alkenyl, aryl or arylalkyl; or a pharmaceutically acceptable salt thereof.

In addition, in accordance with the present invention, a method is provided for treating atherosclerosis wherein a compound of the invention as defined above is administered to a patient in need of treatment.

It is believed that the compounds of the invention function as anti-atherosclerotic antioxidants through inhibition of LDL lipid oxidation product formation.

Pharmaceutically acceptable salts of compounds of formula I include salts such as the hydrochloride salt, hydrobromide salt, methanesulfonic acid salt, tartaric acid salt and the like.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl, cyclododecyl and cyclohexenyl, any of which groups may be optionally substituted with 1 to 4 substituents such as halogen, alkyl, alkoxy, hydroxy, aryl, aryloxy, arylalkyl, aryloxyalkyl, cycloalkyl, alkylamido, alkanoylamino, oxo, acyl, arylcarbonylamino, amino, nitro, cyano, thiol and/or alkylthio.

The term "aryl" or "Ar" as employed herein alone or as part of another group refers to monocyclic and bicyclic aromatic groups containing 6 to 10 carbons in the ring portion (such as phenyl or naphthyl) and may optionally include 1 to 3 additional rings fused to Ar (such as aryl, cycloalkyl, heteroaryl or cycloheteroalkyl rings) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl.

The term "aralkyl", "arylalkyl" or "aryllower alkyl" as used herein alone or as part of another group refers to alkyl groups as discussed above having an aryl substituent, such as benzyl or phenethyl, or naphthylpropyl.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl and/or aryl.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group refers to alkyl, alkenyl, aryl or aralkyl, as defined herein, each linked to a carbonyl

group.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol and/or alkylthio.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

Preferred are compounds of formula I wherein $R^1$ and $R^2$ are each lower alkyl, preferably methyl or ethyl, and $R^3$, $R^4$ and $R^5$ are each hydrogen.

The compounds of the invention may be prepared starting with amine II

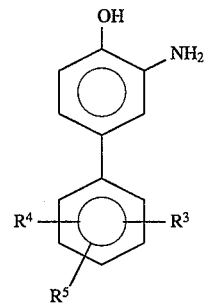

wherein $R^1$, $R^2$, $R^3$, $R^4$ and $R^5$ are as defined hereinbefore, which starting material is known in the art or may be prepared by one skilled in the art employing conventional procedures.

Compounds of formula I where $R^1$ and $R^2$ are each methyl may be prepared as follows.

A solution of amine II in dry alcohol solvent such as methanol, is treated with excess formaldehyde under an inert atmosphere such as argon, at a temperature within the range of from about 20° to about 35° C., preferably at room temperature. The resulting solution is hydrogenated by treatment with hydrogen in the presence of a hydrogenating catalyst such as Pd/C to provide compounds of formula I where $R^1$ and $R^2$ are methyl.

Alternatively, compounds of formula I where $R^1$ and $R^2$ are methyl may be prepared by reductive amination of II with formaldehyde in an alcoholic solvent such as methanol or ethanol, acetonitrile or THF, optionally in the presence of water, in the presence of a borohydride reagent, such as $NaBH_3CN$, $NaB(OAc)_3H$ or $NaBH_4$, optionally in the presence of an acid (for example, HCl or acetic acid) or a Lewis acid (for example $TiO(i-C_3H_7)_4$).

Compounds of formula I where $R^1$ and $R^2$ are the same, but are other than methyl may be prepared by the above methods by substituting for formaldehyde a higher or substituted aldehyde or ketone.

Compounds of formula I where $R^1$ and $R^2$ are the same or different may be prepared by sequential reductive amination or hydrogenation of II as outlined below, using limiting amounts of $R^{1a}COR^{1b}$ to provide IA, followed by $R^{2a}COR^{2b}$ to provide IB'. $R^{1a}$ and $R^{1b}$ are independently any of the $R^1$ groups, and $R^{2a}$ and $R^{2b}$ are independently any of the $R^2$ groups, at least one of $R^{1a}$ and $R^{1b}$ or $R^{2a}$ and $R^{2b}$ being other hydrogen.

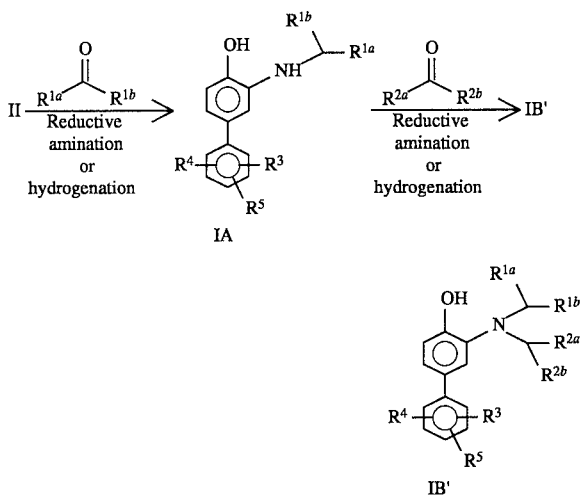

The compounds of the invention may be administered to mammalian species, such as dogs, cats, humans, etc., and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the compounds of the invention in dosages in an amount within the range of from about 1 to 2000 mg per day in single or divided doses, and preferably from about 4 to about 200 mg per day in single or divided doses.

A preferred oral dosage form, such as tablets or capsules, will contain the compound of the invention in an amount of from about 0.5 to about 100 mg, preferably from about 5 to about 80 mg, and more preferably from about 10 to about 40 mg.

Tablets of various sizes can be prepared, e.g., of about 1 to 2000 mg in total weight, containing the active substance in the ranges described above, with the remainder being a physiologically acceptable carrier or other materials according to accepted pharmaceutical practice. These tablets can, of course, be scored to provide for fractional doses. Gelatin capsules can be similarly formulated.

Liquid formulations can also be prepared by dissolving or suspending active substances in a conventional liquid vehicle acceptable for pharmaceutical administration so as to provide the desired dosage in one to four teaspoonsful.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, water, alcohol or the like as the carrier, glycerol as solubilizer, sucrose as sweetening agent, methyl and propyl parabens as preservatives, a dye and a flavoring such as cherry or orange.

Some of the compounds of the invention described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for atherosclerosis remains or the symptoms continue. Sustained release forms of such formulations which may provide such amounts biweekly, weekly, monthly and the like may also be employed. A dosing period of at least one to two weeks or until atherosclerosis has regressed is required to achieve minimal benefit.

The following Examples represent preferred embodiments of the invention.

EXAMPLE 1

3-(Dimethylamino)[1,1'-biphenyl]-4-ol

A. 3-Amino[1,1'-biphenyl]-4-ol

The title compound is commercially available.

B. 3-(Dimethylamino)[1,1'-biphenyl]-4-ol

A suspension of 301.5 mg (1.62 mmol) of 3-amino[1,1'-biphenyl]-4-ol in 10.0 mL of dry MeOH at room temperature under argon was treated with 305 μL (4.05 mmol, 2.5 eq.) of 37% aqueous formaldehyde. After 30 minutes, the resulting solution was hydrogenated by adding 75 mg of 10% palladium on carbon and stirring under a hydrogen balloon for three hours. Filtration through Celite and evaporation of the filtrate yielded 335.8 mg of a gray solid. Purification by flash chromatography on 35 g of silica gel, eluted with 1:3 THF:petroleum ether provided 310.2 mg (90%) of the desired product as a white solid.

m.p. 85°–86° C.

TLC Silica gel (2:8 THF:Hex) $R_f$ 0.31.

IR(KBr) 3430, 3067, 3035, 2993, 2948, 2835, 1600, 1524, 1492, 1456, 1446, 1376, 1292, 1229, 1163, 773, 756, 694 cm$^{-1}$.

$^1$H-NMR(CDCl$_3$) δ7.2–7.6 (m, 7H, PhH, ArH) (270 MHz) 7.00 (d, 1H, j=8.5 Hz, (o—OH)ArH) 2.70 (s, 6H, CH$_3$) ppm.

Mass Spec (CI-H$_2$O,+ ions) m/e 214 (M+H), 198, 184.

Anal. Calc''d for C$_{14}$H$_{15}$NO (M.W. 213.281): C, 78.84; H, 7.09; N, 6.47

Found: C, 78.73; H, 7.19; N, 6.33.

The following compounds of the invention may be prepared employing procedures as described hereinbefore.

10. Esterbauer, H., et al "Continuous monitoring of in vitro oxidation of human low density lipoprotein", (1989) Free Radic. Res. Commun. 6: 67–75.

11. Burton, G. W., et al "Autooxidation of biological molecules. 1. The antioxidant activity of vitamin E and related chain-breaking phenolic antioxidants in vitro" (1981) J. Am. Chem. Soc. 103: 6472–6477.

1. PROCEDURES

A. Primary In Vitro Screen Using Human LDL

This procedure determined the ability of test compounds added directly to LDL to inhibit the initial rate of LDL lipid oxidation monitored by conjugated diene content. The initial rate of conjugated diene formation was approximately linear with respect to time for approximately 2 hours under the conditions employed, prior to the end of the lag phase

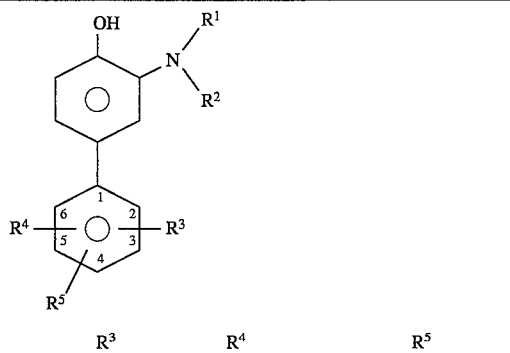

| Ex. No | $R^1$ | $R^2$ | $R^3$ (position) | $R^4$ (position) | $R^5$ (position) |
|---|---|---|---|---|---|
| 2 | CH$_3$ | CH$_3$ | CH$_3$ (3) | H | H |
| 3 | CH$_3$ | (CH$_3$)$_2$C=CH—CH$_2$— | H | H | H |
| 4 | C$_2$H$_5$ | CH$_3$ | Cl (3) | Cl (5) | H |
| 5 | C$_2$H$_5$ | C$_2$H$_5$ | H | H | H |
| 6 | C$_6$H$_5$CH$_2$ | C$_6$H$_5$CH$_2$ | H | H | CH$_3$ (4) |
| 7 | H | CH$_3$ | CH$_3$ (3) | CH$_3$ (5) | CH$_3$O (4) |
| 8 | CH$_3$ | CH$_3$ | H | C$_6$H$_5$CH$_2$ (5) | H |
| 9 | n-C$_3$H$_7$ | C$_6$H$_5$CH$_2$ | H | —CH=CHCH$_3$ (5) | H |
| 10 | n-C$_4$H$_9$ | CH$_3$ | H | C$_6$H$_5$ (5) | H |
| 11 | C$_6$H$_5$CH$_2$ | CH$_3$ | C$_6$H$_5$CH$_2$ (3) | H | H |

EXAMPLE 2

The following experiment was carried out to show the effectiveness of the compound of the invention of Example 1 in treating atherosclerosis.

The initial and later stages of LDL oxidation can be distinguished kinetically in vitro by measuring the formation of lipid conjugated diene oxidation products (ref. 10). By analogy to the behavior of antioxidants in simple single-phase systems (ref. 11), in vitro test systems were established to quantitate the protective effects of pure chemical compounds on Cu$^{++}$-dependent LDL oxidation initial rate and lag phase. Both in vitro and ex vivo methods were employed to incorporate compounds into LDL. The magnitude of the decrease in the initial rate of conjugated diene formation was used as an estimate of the intrinsic LDL antioxidant potency of the test compound. The magnitude of the increase in lag time for the propagation phase of the oxidation chain reaction was used as an estimate of the effective concentration within LDL of the test compound. By this approach, quantitative estimation of the LDL antioxidant activity of compounds was used to identify chain-terminating antioxidants appropriate for testing in an in vivo atherosclerosis animal model.

characterized by rapid propagation of the radical chain reaction and a corresponding large increase in conjugated diene content of the LDL sample. In the assay, aliquots of compounds dissolved in DMSO (and DMSO vehicle controls) were directly added to isolated human LDL (600 μg protein/mL) in Buffer 1 (10 mM HEPES, 150 mM NaCl, pH 7.2), and incubated at 37° for 60 min. Duplicate samples were then subjected to controlled oxidation by addition of CuSO$_4$ (10 μM) and incubation at 37° for 0 or 90 min. The reaction was quenched by diluting with 5 volumes of buffer 1 plus EDTA (20 μM final) at 0°–4°. The conjugated diene levels in the LDL samples, a quantitative indicator of lipid peroxidation rate and extent, was determined spectrophotometrically by absorbance at 234 nm for each sample at 0 min and at 90 min time points of the CuSO$_4$ incubation. From these data, the rate of formation of LDL lipid conjugated diene equivalents (nmol/min/mg) in treated samples vs. controls was calculated. Results are given in Table 1; a decrease vs. control reflects an active antioxidant.

TABLE 1

LDL oxidation initial rate inhibition by
test compounds (primary screen)
Compounds were directly added to isolated
human LDL at the concentration indicated, and the
initial rate of $Cu^{++}$-dependent formation of
conjugated dienes was assayed. BHA is butylated
hydroxyanisole.

| compound | conc μM | % of control |
|---|---|---|
| Example 1 | 0.30 | 66.2 |
|  | 1.0 | 42.2 |
|  | 3.0 | 34.0 |
|  | 10 | 1.7 |
| probucol | 1.0 | 79 |
| BHA | 1.0 | 16 |

B. Secondary In Vitro Screen With Human LDL

A plasma incorporation technique was used in this procedure to test for the partitioning of a compound into LDL and its retention during LDL isolation by ultracentrifugation and dialysis. The antioxidant activity remaining in LDL was then assayed by measuring the initial rate of $Cu^{++}$-dependent conjugated diene formation, and the lag time before extensive formation of conjugated diene oxidation products. Incorporation of test compounds into LDL in vitro was achieved by addition of an aliquot of compound (final concentration 25 μM) in DMSO to aliquots of pooled human plasma previously dialyzed overnight in buffer 1 (10 mM HEPES, 150 mM NaCl, pH 7.2) and adjusted to d=1.019 with solid KBr, and incubating for 60 min at 37°. LDL was then isolated from plasma as the (d=1.09 to d=1.063 g/ml) fraction by standard sequential flotation techniques using KBr solution discontinuous density gradients in an ultracentrifuge by a method adapted from the original procedure of Havel (J. Clin. Invest. 34:1345). The isolated LDL was dialyzed for 1 hour into buffer 1, and aliquots were added to cuvettes at 100 μg protein/ml in buffer 1. Oxidation reactions were initiated with $CuSO_4$ (2.5 μM) at 20°. The LDL initial oxidation rate and lag time were measured by continuous monitoring of absorbance at 234 nm in a Beckman DU-7500 spectrophotometer. The initial oxidation rate was calculated as the slope of the linear regression curve of $A_{234}$ vs. time over the first ~60 min. Percent of control was calculated for test compound vs. DMSO vehicle controls. Lag time was calculated as the time corresponding to the maximum value of the first derivative of the $A_{234}$ vs. time curve. The value of the lag time from the $A_{234}$ vs. time curve for test compounds compared to vehicle control was expressed as percent of control. Results are given in Table 2; a decrease vs. control in the initial rate, and an increase vs. control in the lag time, reflect an active antioxidant.

TABLE 2

LDL oxidation initial rate inhibition and
lag time extension by test compounds after
incorporation of compounds in vitro (secondary
screen)
Compounds were incorporated into LDL in vitro
by the plasma incorporation technique and dialyzed
prior to assay of initial rate and lag time by $Cu^{++}$-
dependent conjugated diene kinetics.

| compound | initial rate % of control | lag time % of control |
|---|---|---|
| Example 1 | 17.9 | 237 |
| probucol | 17.6 | 293 |
| BHA | 11.0 | 239 |

C. Ex Vivo LDL Oxidation Susceptibility Assay In Hamsters

Compounds were administered orally to hamsters for 2 weeks using the same diet described for the atherosclerosis studies (part D.) At 2 weeks, hamsters were fasted overnight, blood was collected, and LDL was isolated as described above (part B). The same assay methods described above (part B.) were then used to obtain ex vivo LDL oxidation initial rate and lag time values. Results are given in Table 3; a decrease vs. control in the initial rate, and an increase in the lag time, reflect an active antioxidant. The data show that the Example 1 compound of the invention was markedly more active in this model than the reference agents probucol and BHA.

TABLE 3

Ex vivo LDL antioxidant activity of test
compounds after 2 weeks oral administration to
hamsters
Compounds were administered in diet for 2
weeks to hamsters at 60 mg/kg/day. LDL isolated from
the hamsters was used to assay initial rate and lag
time by $Cu^{++}$-dependent conjugated diene kinetics.
Mean values from 4 to 6 hamsters per group are shown.

| compound | dose mg/kg/day | initial rate % of control | lag time % of control |
|---|---|---|---|
| Example 1 | 60 | 17 | 482 |
| probucol | 120 | 70 | 141 |
| BHA | 60 | 77 | 116 |

D. In Vivo Atherosclerosis Model in Hamsters

Atherosclerosis in hamsters is confined initially to a lesion prone area along the inner curvature of the aortic arch. Early atherogenesis in this region is characterized by the infiltration of monocytes which become lipid-filled macrophage foam cells, which can develop into complex fibrous atheromas. Antioxidants selected from primary and secondary in vitro screens and ex vivo assays were tested for their ability to inhibit macrophage foam cell lesion formation in hamsters in 10 weeks studies. Lesion size was assayed by video microscopy/image analysis of histological specimens of the aortic arch stained with the lipophilic dye, oil red O. Hamsters were maintained on a diet deficient in vitamins E, C, and K/menadione, selenium, and carotenoids, and supplemented with vitamin E-stripped corn oil (10%) and cholesterol (0.4%). This diet amplified oxidant stress while only moderately elevating plasma cholesterol and LDL levels. Test compounds were administered in this diet fed ad libitum for 10 weeks. The dosages are given as mg/kg/day based on food consumption measurements and weight of the animals at the end of the 10 week dosing period. The compounds did not affect plasma cholesterol or LDL levels. Results are given in Table 4; a decrease in lesion size relative to control indicates an effective anti-atherosclerotic agent. The data show that the Example 1 compound of the invention was markedly more effective than the reference agent probucol.

TABLE 4

Inhibition of aortic foam cell atherosclerosis lesion formation in vivo by oral administration of test compounds for 10 weeks in hamsters
Compounds were administered in diet for 10 weeks to the indicated number of hamsters. Atherosclerosis foam cell lesion size was assayed by microscopy/video image analysis of oil red O stained histologic specimens of the aorta. The table gives the mean ± SEM lesion size values as percentage of control group mean values.

| compound | dose mg/kg/day | n | aortic lesion size % of control | p |
|---|---|---|---|---|
| Example 1 | 60 | 12 | 46.2 ± 6.2 | 0.004 |
|  | 3 | 12 | 71.7 ± 13.7 | 0.17 |
| probucol | 120 | 12 | 59.4 ± 6.4 | 0.02 |

What is claimed is:

1. A method for treating atherosclerosis, which comprises administering to a patient in need of treatment a therapeutically effective amount of a compound having the structure

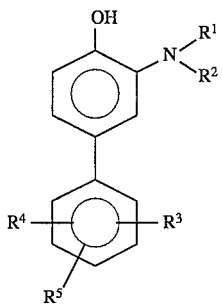

wherein $R^1$ and $R^2$ independently hydrogen, lower alkyl, or arylalkyl, at least one of $R^1$ and $R^2$ being other than hydrogen; and $R^3$, $R^4$ and $R^5$ are independently hydrogen, halo, alkoxy, lower alkyl, lower alkenyl, aryl or arylalkyl; or a pharmaceutically acceptable salt thereof, wherein lower alkyl as employed alone or as part of another group includes both straight and branched chain hydrocarbons optionally substituted with 1 to 4 substituents which are halo, $CF_3$, alkoxy, aryl, aryloxy, aryl(aryl), diaryl, arylalkyl, arylalkyloxy, alkenyl, cycloalkyl, cycloalkylalkyl, cycloalkylalkyloxy, amino, hydroxy, acyl, heteroaryl, heterparyloxy, heteroarylalkyl, heteroarylalkoxy, aryloxyalkyl, aryloxyaryl, alkylamido, alkanoylamino, arylcarbonylamino, nitro, cyano, thiol and/or alkylthio; aryl as employed herein alone or as part of another group refers to monocyclic and bicyclic aromatic groups which optionally include 1 to 3 additional rings fused to Ar which additional rings include aryl, cycloalkyl, heteroaryl or cycloheteroalkyl rings, and aryl may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylazo, heteroarylalkyl, heteroarylalkenyl, heteroarylheteroaryl, heteroaryloxy, hydroxy, nitro, cyano, amino; substituted amino wherein the amino includes 1 or 2 substituents which are alkyl, aryl or any of the other aryl compounds mentioned above; thiol, alkylthio, arylthio, heteroarylthio, arylthioalkyl, alkoxyarylthio, alkylcarbonyl, arylcarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl.

2. The method as defined in claim 1 where in the compound administered, $R^1$ and $R^2$ are each independently lower alkyl.

3. The method as defined in claim 1 wherein the compound administered has the structure

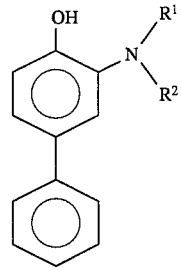

wherein $R^1$ and $R^2$ are independently lower alkyl.

4. The method as defined in claim 3 wherein $R^1$ and $R^2$ are each methyl.

5. The method as defined in claim 1 wherein the treatment for atherosclerosis is carried out by inhibiting LDL oxidation.

6. The method as defined in claim 1 wherein the compound administered is 3-(dimethylamino)[1,1'-biphenyl]-4-ol.

* * * * *